(12) United States Patent
Demura et al.

(10) Patent No.: US 8,878,005 B2
(45) Date of Patent: Nov. 4, 2014

(54) METHOD FOR PROMOTING THE FORMATION OF SECONDARY CELL WALL OF PLANT

(75) Inventors: Taku Demura, Yokohama (JP); Satoshi Endo, Yokohama (JP); Shigeru Sato, Kameyama (JP); Nobuyuki Nishikubo, Kameyama (JP)

(73) Assignee: Riken, Saitama (JP)

( * ) Notice: Subject to any disclaimer, the term of this patent is extended or adjusted under 35 U.S.C. 154(b) by 100 days.

(21) Appl. No.: 13/259,107

(22) PCT Filed: Mar. 31, 2010

(86) PCT No.: PCT/JP2010/055871
§ 371 (c)(1),
(2), (4) Date: Jan. 17, 2012

(87) PCT Pub. No.: WO2010/114024
PCT Pub. Date: Oct. 7, 2010

(65) Prior Publication Data
US 2012/0110699 A1    May 3, 2012

(30) Foreign Application Priority Data

Mar. 31, 2009 (JP) ................... 2009-086922

(51) Int. Cl.
C12N 15/82 (2006.01)
A01H 5/00 (2006.01)
A01H 5/10 (2006.01)
C07K 14/415 (2006.01)

(52) U.S. Cl.
CPC ........ *C12N 15/8246* (2013.01); *C12N 15/8218* (2013.01); *C12N 15/8261* (2013.01); *C07K 14/415* (2013.01); *C12N 15/8223* (2013.01); *C12N 15/8226* (2013.01)
USPC .......................................... 800/284; 800/298

(58) Field of Classification Search
None
See application file for complete search history.

(56) References Cited

U.S. PATENT DOCUMENTS 6,005,092 A    12/1999    Shoseyov et al.

FOREIGN PATENT DOCUMENTS

| JP | 2003-509009 A | 3/2003 |
|----|----|----|
| JP | 2006-246852 A | 9/2006 |
| JP | 2006-526990 A | 11/2006 |
| JP | 4068152 B2 | 3/2008 |
| JP | 2008-178422 A | 8/2008 |
| WO | WO 98/00549 A1 | 1/1998 |
| WO | WO 00/71670 A2 | 11/2000 |
| WO | WO 2005/001051 A2 | 1/2005 |

OTHER PUBLICATIONS

Demura et al. 1994. Novel vascular cell-specific genes whose expression is regulated temporally and spatially during vascular system development. Plant Cell. 6:967-981.*
Endo et al. 2005. Analysis of ZeTED6 and ZeTED7 genes with unknown functions, which are expressed in the tracheary element differentiation process, at the level of cell or organism. Summ. Meet. Japanese. Soc. Plant Phys. p. 1.*
Guo et al. 2004. Protein tolerance to random amino acid change. PNAS. 101(25):9205-9210.*
Igarashi et al. 1998. Expression of the Zinnia TED3 promoter in developing tracheary elements of transgenic *Arabidopsis*. Plant Mol. Biol. 36:917-927.*
Endo, S., et al., "Kan-jo Yoso Bunka Katei de Hatsugen suru Kino Michi Idenshi ZeTED6 Oyobi ZeTED7 no Saibo Oyobi Kotai Level ni Okeru Kaiseki,k" Dai 46 kai, The Japanese Society of Plant Physiologists Nekai Yoshishu, p. 303, PB180(794), (2005).
Demura et al., "Transcriptional Regulation in Wood Formation", Trends in Plant Science, vol. 12, No. 2, 2007, pp. 64-70.
Evert, "Esau's Plant Anatomy", Meristems, Cells, and Tissues of the Plant Body—Their Structure, Function, and Development, Third Edition, 2006, pp. 255-322.
Goicoechea et al., "EgMYB2, A New Transcriptional Activator from *Eucalyptus* Xylem, Regulates Secondary Cell Wall Formation and Lignin Biosynthesis", The Plant Journal, vol. 43, 2005, pp. 553-567.
Kubo et al., "Transcription Switches for Protoxylem and Metaxylem Vessel Formation", Genes & Development, vol. 19, 2005, pp. 1855-1860.
Mitsuda et al., "The NAC Transcription Factors NST1 and NST2 of *Arabidopsis* Regulate Secondary Wall Thickenings and Are Required for Anther Dehiscence", The Plant Cell, vol. 17, Nov. 2005, pp. 2993-3006.
Zhong et al., "SND1, a NAC Domain Transcription Factor, Is a Key Regulator of Secondary Wall Synthesis in Fibers of *Arabidopsis*", The Plant Cell, vol. 18, Nov. 2006, pp. 3158-3170.

(Continued)

*Primary Examiner* — Anne Kubelik
*Assistant Examiner* — Jeffrey Bolland
(74) *Attorney, Agent, or Firm* — Birch, Stewart, Kolasch & Birch, LLP

(57) ABSTRACT

Provided is a method for increasing the thickness of the secondary cell wall of a plant. A method for increasing the thickness of the secondary cell wall of a plant by using a tracheary element differentiation (TED)-associated protein or a C-terminal fragment of the same, which comprises constructing a transgenic (Tg) plant containing, in an expressible manner, a DNA encoding protein(s) selected from the group consisting of a combination of TED6 with TED7, a C-terminal fragment of TED6, a C-terminal fragment of TED7, and a combination of a C-terminal fragment of TED6 with a C-terminal fragment of TED7, and expressing said DNA in said plant; the Tg plant; and a progeny, a cell, a tissue or a seed of the same.

12 Claims, 4 Drawing Sheets

(56) References Cited

OTHER PUBLICATIONS

Endo, S., et al., "Kan-jo Yoso Bunka Katei de Hatsugen suru Kino Michi Idenshi *ZeTED6*Oyobi *ZeTED7* no. Saibo Oyobi Kotai Level ni Okeru Kaiseki," Dai 46 Kai, The Japanese Society of Plant Physiologists Nekai Yoshishu, p. 303, PB180(794), (2005).

Demura, T., et al., "Novel Vascular Cell-Specific Genes Whose Expression Is Regulated Temporally and Spatially during Vascular System Development," The Plant Cell, vol. 6, pp. 967-981 (1994).

Database GenBank, Acession No. NM 103507, www.ncbi.nlm.nih.gov, Arabidopsis thaliana unknown protein (AT1G43790) mRNA 2008.

Database GenBank, Accession No. NM_124269, www.ncbi.nlm.nih.gov, Arabidopsis thaliana hydroxyproline-rich glycoprotein family protein (AT5G48920) mRNA 2008.

Endo, S., et al., "Identifying New Components Participating in the Secondary Cell Wall Formation of Vessel Elements in *Zinnia* and *Arabidopsis*," The Plant Cell, vol. 21, pp. 1155-1165 (2009).

* cited by examiner

Fig. 1
A
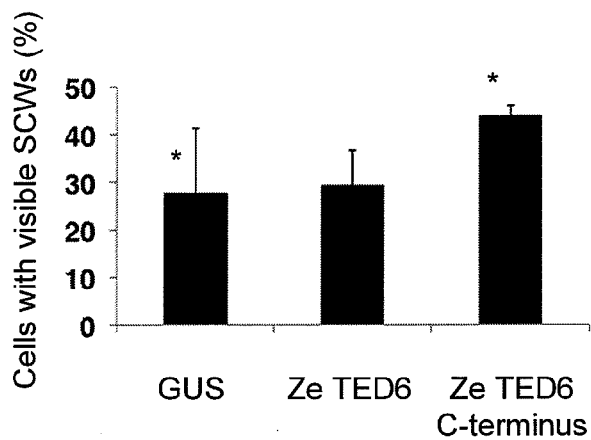
B
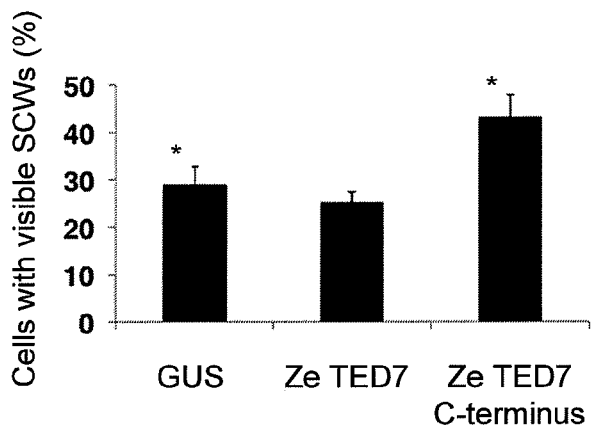
C
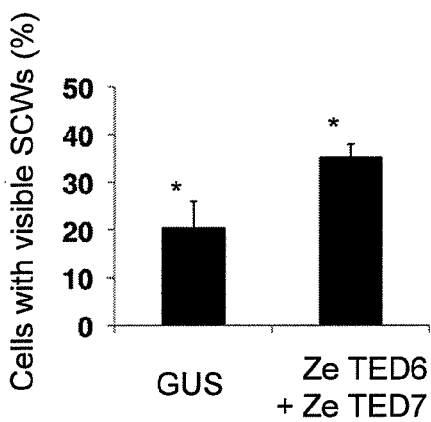

```
Ze TED7-1         MASPLSQSVFPHFPPPSPAATPPAPTTPSTPPPHFISPPHSVPPPSPPHPVSPPPHTVPPPSPPHPVSP
Ze TED7-2         MASHLSQSLFPHFPPPSPAATPPAPTTPSTPPPHFISPPHSVPPPSPPHFISPPHSVPPPSPPHSVPPPLHPVPPPLPPHSVP
At5g48920 / At TED7                                                                                    MAP
eugene3.00070382
fgenesh1_pg.C_LG_V000008                                   MAPLDNYDYNFPYFPLPPPHNPPSPPKVVPPHNYPSPPKGSPPHNPPPH
Os08g0108300      MTFNPGSPGFGFPFFYPPNPNPYAPLNPNAPKPPVMPPRPQAPPPQRFPPPPAPPIRPPSPPGRAPPPGRAPPPSQA At1g43790 / At TED6                                                                                MASTDSV
eugene3.00020671                                                    MAASNNLDFPYSPPPPSPHSFQPPPSPPHVRPPPPHIRPPPP
Ze TED7-1         PPPHTVPPPSPPHPVFPPPHTVPPPSPPHFVPPPPNMVPPPSPPHANPPPPPHSVPPPPPHTVPPPPPHIIPPPAHALSPPPHII
Ze TED7-2         PPSHTVPPPSPPHVSPPPHTVPPPSPPHVSPPPHTVPPPSPPHHVSPPPHTVPPPSPHFVPPPNTVPPPAPHFVPPPPPYII
At5g48920 / At TED7 MAASVEYFPYYSPPSHQHPLPSPVPPPFSHISPPPPPFSPPHHPPPHFSPPHQPPPSYFHPHPPPSPYHPHQPPPPHV
eugene3.00070382  TNNYDYNFYFPLPPHNNPSPPKVAPPHSSPSPDNVSPPHNFPPPHITPPSPKVPPPHHITPPTHPHPPPHIPPPHVI
fgenesh1_pg.C_LG_V000008 IIPSPPKVVPPHNYPSPPKGSPPHNPPPHIKPSPPKVPPPHHPITPPSPPFVPATPPNHPFHPPPHHIPPSPPHIIPPAPSHVI
Os08g0108300      PPPPRRAPPPPPALPPPPPPRAPPPPSMPPPPPPRRAPPPPATPPPPPRRAPPPPSPPIRPPPFPTPRPYAPPPSHPLAPPPHISP MATIFIVFVSFGCVFVLGIAAFVLCCLIKKWKCSKALEKNEMVHVDQHLQVHENILQGPNGMKTVAITVDDDLHVDE
Ze TED6           YRPTPTPDHDTTVWVVFVSLGCVMFLAFLAFVIWFLIKKRSRKHRERSEAVRVDEHFKMKEAIVEGPNGQKSVVLSVEDDVKIEDA
At1g43790 / At TED6 LPPAPSPSNTTVIVIVFSVGGLIFLAFLAAAALCFFIKKKKKKTVEETDIVHVHEHLKVKEAIVEGPHGPKAVVLEIVDDVHIGEE
eugene3.00020671  PPPPSPSNHSTTIVIFVSGGVFFLAFAMAALWCFLKKKKKMVQKAENTHFDEHRKVTERIEQGPHGTETAILSVEDDIHIEED
Ze TED7-1         PPPPPSPSNHSTTIVIFVSCGGVFFLAFAMAALFCFLKKKKKKMVRKAENIHFDEHRKVTERIEQGPHGTETAILSVEDDIHIEED
Ze TED7-2         LPPPPPTPAPGHHVTIVVVISLGSLFFLAFLAAALFCYLKKRRKSSTKAEIIEFDEHLKVQETIVQGPHGEQTRVMLEEDIHLVED
At5g48920 / At TED7 PPPPPPTPGHHSTVIIVFVSLGGLFFLAFLSVALCCFIKKKKKKTVQKTEILEFDEHTKVQEAIVPGPHGEKITVLNIEEDVHLVEE
eugene3.00070382  PPPPPTPGHHSTVIIVFVSLGGLFFLAFLSVALCCFIKKKKKKTVQKTEILEFDEHTKVQEAIIPGPHGEKITVLNIEEDVHLVEE
fgenesh1_pg.C_LG_V000008 PPPPPTPGHHSTVIIVFVSFGGLILLLACLAALFCWHHKRRETERKAEVHNLSGHVHVHKATESGPSGAKATVLSIDEDLKFQEV
Os08g0108300      PAPVPPPSPPHIVIIVVFSFGGLILLLACLAALFCWHHKRRETERKAEVHNLSGHVHVHKATESGPSGAKATVLSIDEDLKFQEV
                        *             H              GP G          *D *    *)

Ze TED6           EECVKNEKLGTASTSKA (SEQ ID NO: 1)
At1g43790 / At TED6 IKREEKDLKKDGGVGSSVVSRS (SEQ ID NO: 4)
eugene3.00020671  IKEEEKVGEGLHAKAIEGNACTVDQLAAPSSSGSNNHSRLEHKA (SEQ ID NO: 6)
Ze TED7-1         IKKSELENFRKGLHLNYGNTYNIDTGKPSSSFGHHYLHG (SEQ ID NO: 2)
Ze TED7-2         IKKSEIEDFRKGLHLNYGNTYNIDTGKPSSSFGHHYLHG (SEQ ID NO: 3)
At5g48920 / At TED7 IHKTEKLSRPSHLSSTGRHAIDISDPNHHFTEQKS (SEQ ID NO: 5)
eugene3.00070382  IKKNEKLTEGSHIKSAHDRPLYSDIATPSSQYNQHHLEHKV (SEQ ID NO: 7)
fgenesh1_pg.C_LG_V000008 IKKNEKLAEGSHIKLAHDHPLDSDIATSSSRSNQQHLEHKV (SEQ ID NO: 8)
Os08g0108300      AGESSSAAGAGSHHTPWSWHRQQEGKAENCAELINVTEHIHVDEKIVSGPGQKIEILSEDEDIRFEEEGRKEKGDQRSKTRITKT (SEQ ID NO: 9)
```

METHOD FOR PROMOTING THE FORMATION OF SECONDARY CELL WALL OF PLANT

This application is the national stage of international Application PCT/JP2010/055871, filed in Japan on Mar. 31, 2010, and claims priority under 35 USC §119(a)-(d) of Japanese Application 2009-086922, filed in Japan on Mar. 31, 2009.

TECHNICAL FIELD

The present invention relates to a protein having the function of promoting the formation of wood fiber secondary cell walls of plants, DNA encoding the protein, and the use thereof.

BACKGROUND ART

Human beings have long used woody biomass such as trunks, roots, leaves, and branches in various industrial fields, including paper-making, construction, feedstuff production, fuel production, and the like. Industries in which woody biomass is utilized are realized again in view of the improvement of global environmental issues because they enable the use of sustainably-usable resources in the future. Thus, such industries are expected to be recycling-oriented industries, which utilize carbon sources instead of current fossil resources. Hence, the afforestation industries mainly for fast-growing trees of the genus Eucalyptus, the genus Acacia, and the like are promoted throughout the world in order to stably and sustainably secure woody biomass.

Woody biomass is composed of vessel cells and wood fiber cells existing in the secondary xylem of plant stems. These cells are both characterized by the formation of secondary cell walls within the cells, which are composed of cellulose, hemicellulose and lignin. Wood fiber cells which account for most of the secondary xylem are used as woody biomass in industrial fields (Non-patent Document 1). The amount of secondary cell walls (the degree of thickness) of the wood fiber cells is very important because it influences the amount of biomass or the physical properties of wood fibers.

In recent years, bioenergy production and biofinery using woody biomass have become increasingly popular, as is well known. It is very beneficial to thicken the secondary cell walls to increase the amount of biomass in view of improvement of the productivity and cost reduction. Also, when woody biomass is regarded as a raw material for conventional paper-making, it is very beneficial to thicken the secondary cell walls to increase the amount of biomass in view of improvement of the productivity and cost reduction for bulky paper and the like, for which wood fibers having thick secondary cell walls and high Runkel ratio (secondary cell wall-to-lumen ratio) levels are required.

In concert with the future development of afforestation program, the formation of secondary cell walls of wood fiber cells as major source of woody biomass is promoted to change the amount of biomass (cellulose, hemicellulose, and lignin) and to change the morphology of wood fibers (e.g., the Runkel ratio). Thereby, future use for energy or expanded applications as industrial raw materials can be expected. Therefore, the development of a method for promoting the formation of secondary cell walls of wood fiber cells is very important for realizing more effective and efficient production of woody biomass on a global scale.

Several methods for promoting the secondary cell wall formation have become known to date (Patent Documents 1 to 5 and Non-patent Documents 2 to 5). However, they cannot be put to practical use because many of them relate to the promotion of the formation of secondary cell walls of plant cells other than wood fibers, and the amounts of cells and secondary cell walls resulting from the promotion are extremely low. Further, although there are techniques for promoting the formation of secondary cell walls of wood fiber cells, they cannot be practically used because adverse effects such as dwarfing are observed. As described above, it is difficult to promote the formation of secondary cell walls of wood fiber cells using the currently known techniques.

The present inventors have found many genes whose expression is specifically induced upon the formation of vessel cells (Non-patent Document 6). The group of genes found by the present inventors comprises many genes of unknown functions, and these genes are considered to play some roles in vessel formation. Vessel cells and wood fiber cells are highly analogous to each other in that both cells form secondary cell walls inside the cells, and they both are said to originate from tracheids. Therefore, it is considered that the analysis of the functions of these genes can enable the control of the secondary cell wall formation, not only for vessel cells, but also for wood fiber cells. However, there has been no such technique or finding.

PRIOR ART DOCUMENTS

Patent Documents

[Patent Document 1] JP Patent No. 4068152
[Patent Document 2] JP Patent Publication (Kohyo) No. 2003-509009 A
[Patent Document 3] JP Patent Publication (Kokai) No. 2006-246852 A
[Patent Document 4] JP Patent Publication (Kohyo) No. 2006-526990 A
[Patent Document 5] JP Patent Publication (Kokai) No. 2008-178422 A

Non-Patent Documents

[Non-patent Document 1] Evert, RF. Esau's Plant Anatomy, Meristems, Cells, and Tissues of the Plant Body: their Structure, Function, and Development. 3rd Ed. New Jersey: John Wiley & Sons, Inc.
[Non-patent Document 2] Kubo et al., 2005 Genes & Dev. 19:1855-1860
[Non-patent Document 3] Goicoechea et al., 2005 The Plant Journal 43:553-567
[Non-patent Document 4] Mitsuda et al., 2005 The Plant Cell 17:2993-3006
[Non-patent Document 5] Zhong et al., 2006 The Plant Cell 18:3158-3170
[Non-patent Document 6] Demura, T. and Fukuda, H., 2007 Trends in Plant Sci. 12:64-70

SUMMARY OF THE INVENTION

Problem to be Solved by the Invention

The present invention has been achieved in view of the aforementioned circumstances. An object of the present invention is to provide a method for using TED6 and TED7, which are genes of unknown functions, and plants in which the secondary cell wall formation is promoted.

Means for Solving the Problem

The present inventors have predicted that TED6 or TED7, which is a tracheary element differentiation (TED)-associated protein of a plant, might be involved in cellulose synthesis and pattern formation of secondary cell walls of plants. However, they have revealed that such a protein alone does not have this function. As a result of further intensive studies, they have completed the invention having the following features.

In summary, the present invention has the following features.

In a first aspect, the present invention provides a method for increasing the thickness of a secondary cell wall of a plant using a TED-associated protein or a C-terminal fragment thereof, comprising producing a transgenic plant that contains, in an expressible manner (that is, so that the genes can be expressed), DNA encoding a protein selected from the group consisting of a combination of TED6 and TED7, a C-terminal fragment of TED6, a C-terminal fragment of TED7, and a combination of a C-terminal fragment of TED6 and a C-terminal fragment of TED7, and causing the expression of the DNA within the plant.

In an embodiment of the above aspect, the above C-terminal fragment of TED6 or TED7 consists of an amino acid sequence lacking the sequence from the N-terminus to the transmembrane domain in the mature amino acid sequence of TED6 or TED7, or, an amino acid sequence containing a deletion, a substitution, or an addition of one or several amino acids on the N-terminal side and/or the C-terminal side of the amino acid sequence lacking said sequence.

Here, "several" indicates an integer of 10 or less; that is, an integer of 2 to 10.

In a second aspect, the present invention provides a transgenic plant or a progeny plant thereof characterized in that it contains, in an expressible manner, DNA encoding a protein selected from the group consisting of the combination of TED6 and TED7, the C-terminal fragment of TED6, the C-terminal fragment of TED7, and the combination of a C-terminal fragment of TED6 and a C-terminal fragment of TED7 as described above, and that the thickness of a secondary cell wall is increased as compared with that of a wild-type plant.

In a third aspect, the present invention further provides cells or tissues derived from the above transgenic plant or progeny plant thereof.

In a fourth aspect, the present invention further provides seeds of the above transgenic plant or progeny plant thereof.

A part or all of the content disclosed in the description and/or drawings of Japanese Patent Application No. 2009-086922, which is a priority document of the present application, is herein incorporated by reference.

Effects of the Invention

The method of the present invention makes it possible to promote the secondary cell wall formation in wood fiber cells of plants and thus to increase the thicknesses of secondary cell walls. Thickening of secondary cell walls is advantageous in that it can result in an increased amount of biomass.

BRIEF DESCRIPTION OF THE DRAWINGS

FIG. 1 shows the effects of the overexpression of Ze TED6, Ze TED7, and C-terminal fragments thereof on the secondary cell wall formation of *Zinnia elegans* cells. The vertical axis indicates the percentage (%) of cells having visible secondary cell walls. FIG. 1A shows the overexpression of full-length Ze TED6 and the C-terminal fragment ($^{27}$Leu-$^{95}$Ala of SEQ ID NO: 1) of Ze TED6. FIG. 1B shows the overexpression of full-length Ze TED7-1 and the C-terminal fragment ($^{209}$Trp-$^{300}$Gly of SEQ ID NO: 2) of Ze TED7-1. FIG. 1C shows the co-overexpression of Ze TED6 and Ze TED7. Further, in FIG. 1, GUS (β-glucuronidase) indicates a plant control in which GUS was overexpressed instead of Ze TED6, Ze TED7, or a C-terminal fragment thereof.

In FIG. 2A, bold letters indicate transmembrane domains and underlines indicate the amino acid sequences of the clones Z1943 and Z16653 used in Examples. Os08g0108300 contains two repeated C-terminal domains (FIG. 2A). FIG. 2B shows the two conserved repeated C-terminal domains of Os08g0108300 being divided.

FIG. 3A shows the expression of the At TED6 and At TED7 genes under conditions of transiently induced RNAi. Inverted repeat sequences corresponding to At TED6, At TED7, and both of them were transiently expressed in transgenic *Arabidopsis thaliana* plants under the control of a glucocorticoid-mediated induction system. Total RNAs were extracted from 1-week-old *Arabidopsis thaliana* seedlings after 5 hours of incubation on a growth medium supplemented with 10 μM dexamethasone. AU RT-PCR samples were prepared under the same conditions, except that 25 PCR cycles were employed for At TED6, and 30 PCR cycles were employed for At TED7 and ubiquitin. FIG. 3B to FIG. 3E show the phenotypes of the RNAi lines of the At TED6 and At TED7 genes. Three (3)-week-old transgenic *Arabidopsis thaliana* plants were incubated on a growth medium supplemented with 10 μM dexamethasone for 5 days, so that the inverted repeat sequences were expressed using the glucocorticoid'-mediated induction system. During induction, the effects of RNAi on vessel formation in more slowly developed roots were examined. In FIG. 3B, a bar indicates 50 μm. FIG. 3B shows wild-type Col-0. FIG. 3C shows the At TED7 RNAi line, showing linearly elongated metaxylem vessels which are scalariform. FIG. 3D shows an At TED6-TED7 chimera RNAi line and specifically shows a deletion in linearly elongated metaxylem vessels. FIG. 3E shows an YFP RNAi line and specifically shows metaxylem vessel elements with large pits. Here, "YFP" indicates a yellow fluorescent protein.

EMBODIMENTS FOR CARRYING OUT THE INVENTION (DNA Encoding TED6 and TED7 Proteins)

TED6 and TED7 are both type I membrane proteins associated with the differentiation of tracheary elements such as vessels of plants. These proteins lead to the promotion of the formation of secondary cell walls of vessel cells or wood fiber cells when they are simultaneously overexpressed in plant cells.

In many plant species TED6 and TED7 have a characteristic structure, which is composed of, from the N-terminal side, a proline (Pro)-rich domain, a single transmembrane (TM) domain, and a C-terminal domain. The proline-rich domain is an extracellular domain, while the C-terminal domain is a cytoplasmic domain. In general, it is well known that, among plant extracellular proteins, proline-rich sequences are characteristic of hydroxyproline-rich glycoproteins (HRGPs). In particular, TED7 is assumed to be HRGP, although Ze TED7 lacks a repeat sequence which is typically observed in the HRGP family.

Figure 2:
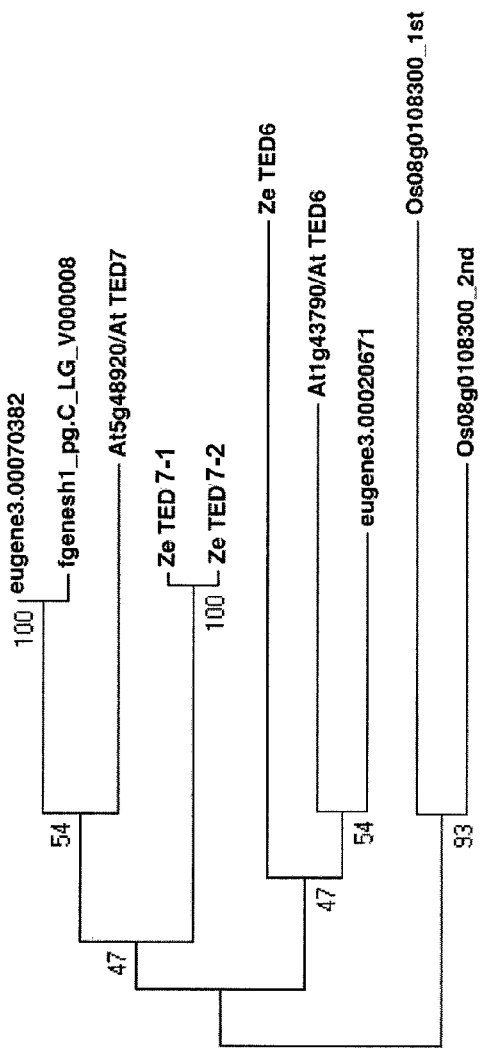
FIGS. 2A-2C show: an alignment (FIG. 2A) of the amino acid sequences of *Zinnia elegans* TED6 and TED7 (that is, Ze TED6 and Ze TED7) and the amino acid sequences of the homologs of *Arabidopsis thaliana, Populus trichocarpa*, and *Oryza sativa*; a dendrogram (FIG. 2B) showing the comparison of conserved regions using MEGA4 (Molecular Evolutionary Genetics Analysis software version 4.0; Tamura, K. et al., (2007) Mol. Biol. Envol. 24: 1596-1599) according to a neighbor-joining method; and the relatively conserved C-terminal regions (FIG. 2C) of the amino acid sequences used for preparation in FIG. 2B.

FIG. 2 shows the alignment of the amino acid sequences of TED6 and TED7 of exemplary plants including *Zinnia elegans*, *Arabidopsis thaliana*, *Populus trichocarpa*, and *Oryza sativa* (FIG. 2A), and the amino acid sequences of relatively conserved C-terminal regions in the above amino acid sequences (FIG. 2C). Although the sequence identity among the TED proteins from plants of different species is low, it is understood that the above exemplary proteins belong to the tracheary element differentiation-associated protein family based on the fact that they have the above characteristic domain structures.

The amino acid sequences of TED6 and TED7 derived from these plants are listed in the Sequence Listing with the following SEQ ID NOS.
*Zinnia elegans* TED6, TED7-1, and TED7-2: SEQ ID NO: 1(AB377514), SEQ ID NO: 2 (AB377515), and SEQ ID NO: 3 (AB377516)
*Arabidopsis thaliana* TED6 and TED7: SEQ ID NO: 4 (At1g43790) and SEQ ID NO: 5 (At5g48920)
*Populus trichocarpa* TED6 and TED7: SEQ ID NO: 6 (eugene3. 00020671) and SEQ ID NO: 7 (eugene3. 00070382), SEQ ID NO: 8 (fgenesh1_pg. C_LG_V000008) (here, the sequences of SEQ ID NOS: 7 and 8 belong to TED7).
*Oryza sativa* TED: SEQ ID NO: 9 (Os08g0108300) ((note) SEQ ID NO: 10 (Os 08g0108300_1st: TERKAEVHNL SGHVHVHKAT ESGPSGAKAT VLSIDEDLKF QEVAG) and SEQ ID NO: 11 (Os08g0108300_2nd: AENKAELINV TEHIHVDEKI VSGPQGQKIE ILSEDEDIRF EEEGR) (here, the sequences of SEQ ID NOS: 10 and 11 are partial sequences prepared by dividing a duplicate domain in the sequence of SEQ ID NO: 9)).

Further, the amino acid residue positions of amino acid sequences of the transmembrane region and the C-terminal domain (FIG. 2A), as well as the relatively conserved C-terminal region (FIG. 2C) in these amino acid sequences can be determined based on the amino acid sequences of SEQ ID NOS: 1-11 and sequences listed in FIG. 2.

Regarding TED6, TED7, and C-terminal fragments thereof that can be used in the present invention, a mutation may be introduced into the wild-type amino acid sequence as long as the capability of a combination of TED6 and TED7, a C-terminal fragment of TED6 or a C-terminal fragment of TED7 to promote the formation of secondary cell walls of vessel cells or wood fiber cells is not lost. Such mutant TED6 and TED7 have 70% or more or 80% or more, preferably 90% or more or 95% or more, and further preferably 98% or more or 99% or more identity with the wild-type amino acid sequence. Amino acid mutation is, for example, deletion, substitution, or addition of 1 or a plurality of (preferably, several) amino acid(s). The substitution is desirably conservative amino acid substitution. The term "conservative amino acid substitution" refers to substitution for an amino acid having a similar property, for example, in terms of structure, electricity, polarity, or hydrophobicity. Such properties can also be classified, for example, based on the similarity of the side chains of amino acids. Amino acids having basic side chains comprise lysine, arginine, and histidine. Amino acids having acidic side chains comprise aspartic acid and glutamic acid. Amino acids having uncharged polar side chains comprise glycine, asparagine, glutamine, serine, threonine, tyrosine, cysteine, and the like. Amino acids having hydrophobic side chains comprise alanine, valine, leucine, isoleucine, proline, phenylalanine, methionine, and the like. Amino acids having branched side chains comprise threonine, valine, and isoleucine. Amino acids having aromatic side chains comprise tyrosine, tryptophan, phenylalanine, and histidine.

DNAs encoding TED6, TED7, and C-terminal fragments thereof as described above can also contain a mutation(s). Examples of such mutation include mutation based on degeneracy of genetic code (i.e., silent mutation), splice mutation, mutation due to polymorphism. Further, examples of the above mutant DNA also include a mutant comprising a nucleotide sequence capable of hybridizing to wild-type DNA under stringent conditions. In this case, the mutant protein encoded by such DNA should have the capability to promote the formation of secondary cell walls of vessel cells or wood fiber cells, in the form of a combination of TED6 and TED7, a C-terminal fragment of TED6, or a C-terminal fragment of TED7. Such capability may be equivalent to or higher than that of the wild-type protein, or may be inferior to that of the wild-type protein. DNAs encoding mutant TED6 and mutant TED7 have 70% or more or 80% or more, preferably 90% or more or 95% or more, and more preferably 98% or more or 99% or more identity with a wild-type mature nucleotide sequence.

Here, examples of stringent conditions include conditions comprising hybridization at about 42° C. to 55° C. with 2 to 6×SSC and one or several rounds of washing at 50° C. to 65° C. with 0.1 to 1×SSC and 0.1% to 0.2% SDS. Such conditions may vary depending on the GC content of template nucleic acid, ionic strength, temperature, and the like, and thus they are not limited to the above specific conditions. Here, 1×SSC consists of 0.15 M NaCl and 0.015 M Na citrate at pH 7.0. In general, stringent conditions are determined so that the temperature is lower by about 5° C. than the melting temperature (Tm) of a specific sequence at specified ionic strength and pH. Here, the term "Tm" refers to the temperature at which 50% of probes complementary to a template sequence hybridize to the template sequence in equilibrium.

For example, site-directed mutagenesis, mutagenesis using PCR, or the like can be preferably employed as a technique for artificially introducing mutation (Sambrook et al., Molecular Cloning A Laboratory Manual, 1989, Cold Spring Harbor Laboratory Press; Ausubel et al., Current Protocols in Molecular Biology, 1994, John Wiley & Sons).

The term "identity" as used herein means, for example, the ratio (%) of the number of identical amino acids or nucleotides to the total number of amino acids or nucleotides observed when two amino acid sequences or nucleotide sequences are aligned with or without introduction of gaps.

Further, homologous sequence search or homology search can be performed using a known algorithm such as BLAST (e.g., BLASTN, BLASTP, and BLASTX) or FASTA.

The amino acid sequences of TED6 and TED7 proteins from plants other than those exemplified above and the nucleotide sequences of DNAs encoding such proteins can be obtained by accessing to web sites at which plant genomes are opened to the public, such as NCBI (U.S.A.), EBI (Europe), KAOS (Kazusa DNA Research Institute), IRGSP (International Rice Genome Sequencing Project), GrainGenes (U.S.A.), PGDIC (U.S.A.), ForestGEN (Forestry and Forest Products Research Institute).

According to the present invention, specifically, a combination of TED6 and TED7, a C-terminal fragment of TED6, a C-terminal fragment of TED7, and a combination of a C-terminal fragment of TED6 and a C-terminal fragment of TED7 have important functions in promotion of the formation of secondary cell walls of vessel cells or wood fiber cells.

Here, "a combination of TED6 and TED7" can be realized by substantially simultaneous expression of DNAs encoding TED6 and TED7 within a plant or a plant cell followed by the translation into the proteins. In this case, for the expression of the DNAs, the two DNAs may be incorporated into separate vectors in an expressible manner, or the two DNAs may be incorporated in tandem into the same vector in an expressible manner.

Further, "a C-terminal fragment" in "a C-terminal fragment of TED6" or "a C-terminal fragment of TED7" may be composed of a C-terminal domain on the cytoplasmic side of the TED6 or TED7 protein (i.e., a domain having an amino acid sequence that lacks the sequence from the N-terminus to the transmembrane domain in the mature amino acid sequence). Alternatively, the C-terminal fragment may have an amino acid sequence having a deletion, a substitution, or an addition of one or several amino acids on the N-terminal side and/or the C-terminal side in the amino acid sequence of the C-terminal domain. In the latter case, for example, about 1 to 3 amino acid residues from the transmembrane region flanking the C-terminal domain may be added on the N-terminal side of the C-terminal fragment. Alternatively, for example, a portion of the sequence on the C-terminal side (e.g., 10 or less amino acid residues) may be deleted from the amino acid sequence of the C-terminal domain. Usually, it is desirable that the above C-terminal fragment in the present invention contains an amino acid sequence relatively conserved among plants as shown in FIG. 2C, and has the capability to promote the formation of secondary cell walls of vessel cells or wood fiber cells. DNA encoding such a C-terminal fragment can be obtained by performing polymerase chain reaction (PCR) using DNA encoding a TED6 or TED7 protein as a template, and 5' and 3' primers prepared based on a sequence to be amplified in the nucleotide sequence encoding the C-terminal domain (which may optionally contain 1 to 3 amino acid residues on the C-terminal side of the transmembrane region). Subsequently, the thus prepared DNA is incorporated into an appropriate vector.

Regarding a PCR method and conditions therefor, a usual technique is employed, which consists of an amplification cycle comprising about 20 to 40 cycles of denaturation (e.g., 94° C. for 20 seconds to 5 minutes), annealing (e.g., 55° C. for 30 seconds to 1 minute) and elongation (e.g., 72° C. for 30 seconds to 10 minutes) in a PCR buffer and in the presence of thermostable DNA polymerase (e.g., Taq polymerase), a sense primer, an antisense primer, dNTPs (N=A, T, G, C), and template DNA. A specific technique is described, for example, in Ausubel et al., Current Protocols in Molecular Biology, 1994, John Wiley & Sons. Amplification products can be isolated and purified using agarose gel or polyacrylamide gel electrophoresis.

Incidentally, the amino acid sequences of C-terminal fragments of Zinnia elegans TED6 and TED7-1 used in Examples below are the sequence ranging from $^{27}$Leu to $^{95}$Ala in SEQ ID NO: 1 and the sequence ranging from $^{209}$Trp to $^{300}$Gly in SEQ ID NO: 2, respectively.

Furthermore, "a combination of a C-terminal fragment of TED6 and a C-terminal fragment of TED7" can be realized, as in the case of "a combination of TED6 and TED7," by substantially simultaneous expression of DNAs encoding a C-terminal fragment of the TED6 protein and DNA encoding a C-terminal fragment of the TED7 protein within a plant or a plant cell followed by translation into the proteins. In this case, for the expression of the DNAs, the two DNAs may be incorporated into separate vectors in an expressible manner, or the two DNAs may be incorporated in tandem into the same vector in an expressible manner.

The above DNAs and vectors containing them can be produced, for example, by genetic engineering techniques. As the genetic engineering techniques, for example, techniques described in Sambrook et al., Molecular Cloning a Laboratory Manual, 1989, Cold Spring Harbor Laboratory Press; Ausubel et al., Current Protocols in Molecular Biology, 1994, John Wiley & Sons, and the like can be employed.

Briefly, for example, DNA encoding TED6 or TED7 can be amplified from a plant tissue-derived cDNA library by PCR using primers prepared based on known sequences. The DNA is purified, for example, by agarose gel or polyacrylamide gel electrophoresis and then is inserted into an appropriate expression vector in an expressible manner.

Examples of the vector include binary vectors and other vectors. A binary vector contains two about 25-bp border sequences, the right border (RB) and the left border (LB), of Agrobacterium T-DNA, between which a foreign DNA is inserted. Examples of the binary vector include pBI vectors (e.g., pBI101, pBI101.2, pBI101.3, pBI121, and pBI221 (Clontech)), pGA482, pGAH, and pBIG. Examples of other vectors include intermediate plasmids such as pLGV23Neo, pNCAT, and pMON200, and pH35GS which contains the GATEWAY cassette (Kubo et al., 2005, Genes & Dev. 19: 1855-1860). A promoter is ligated to the 5' end of the foreign DNA. Examples of the promoter include a cauliflower mosaic virus (CaMV) 35S promoter, a nopaline synthase gene promoter, a corn ubiquitin promoter, an octopine synthase gene promoter, and a rice actin promoter. Further, a terminator (e.g., a nopaline synthase gene terminator) is inserted at the 3' end of foreign DNA. A selection marker which is required for selection of transformed cells is further inserted into the vector. Examples of the selection marker include drug resistance genes such as a kanamycin resistance gene (NPTII), a hygromycin resistance gene (htp), and a bialaphos resistance gene (bar).

(Production of Transgenic Plant)

An example of a transformation method for introducing the thus constructed vector into a plant is a method using Agrobacterium. A vector can also be introduced using other methods such as a gene gun, electroporation, a viral vector, a floral dip method, a leaf disc method. Plant transformation techniques and tissue culture techniques are described, for example, in Isao Shimamoto and Kiyotaka Okada (supervisors), Shokubutsu Saibou Kougaku Series 15, Model Shokubutsu No Jikken Protocol, Idengakuteki Shuhou Kara Genome Kaiseki Made (Plant Cell Technology Series 15, Model Plant Experimental Protocols, From Genetic Techniques to Genome Analysis), 2001, Shujunsha.

According to a method using a binary vector-Agrobacterium system, plant cells, calluses, or plant tissue sections are prepared and then infected with Agrobacterium, so as to introduce DNA encoding a protein of the present invention into plant cells. Upon transformation, a phenol compound (acetosyringone) may be added to a medium. In particular, in the case of monocotyledons, the cells can be efficiently transformed. Further, as Agrobacterium, Agrobacterium tumefaciens strains (e.g., C58, LBA4404, EHA101, EHA105, and C58C1RifR) can be used.

A transformation medium is a solid medium. For example, a plant culture medium such as an MS medium, a B5 medium, a DKN medium, or Linsmaier & Skoog medium is used as a basal medium. To the medium, 1%-5% saccharide such as maltose, sucrose, glucose or sorbitol, and 0.2%-1% polysaccharide solidifying agent such as agar, agarose, Gelrite or gellan gum can be added. Casamino acids, abscisic acid, auxin or cytokinin such as kinetin, 2,4-D, indoleacetic acid or indolebutyric acid, antibiotic such as kanamycin, hygromycin or carbenicillin, acetosyringone, and the like can be added to the medium. pH preferable for the medium ranges from 5 to 6, for example, pH 5.5 to 5.8. Further, a substance that induces transcriptional activation, such as a steroid hormone (e.g., glucocorticoid, dexamethasone, estrogen, or a derivative thereof), may be added to the medium after transformation.

Specifically, an *Agrobacterium* suspension is prepared by about 4 days of culture in the dark at about 25° C. Plant calluses or tissues (e.g., laminae, roots, stem sections, or growing points) are immersed in the bacterial suspension for several minutes, moisture is removed, and then the resultants are placed on a solid medium for cocultivation. A callus is a mass of plant cells, which can be induced using a callus induction medium from a plant tissue section, a fully ripened seed or the like. The transformed calluses or tissue sections are selected based on a selection marker. In case of calluses, they can subsequently be caused to redifferentiate into adventitious shoots using a redifferentiation medium. Meanwhile, in case of plant sections, calluses can be induced from the plant sections and then induced and caused to redifferentiate into adventitious shoots, or protoplasts can be prepared from the plant sections and then caused to redifferentiate into adventitious shoots after callus culture. The thus obtained adventitious shoots are transplanted into soil after rooting so that they are regenerated into plants.

Further, when a floral dip method is used, the method is performed, for example, as described by Clough and Bent et al. (Plant J. 16, 735-743 (1998)), for example, as follows: an *Agrobacterium* suspension is prepared by about 4 days of culture in the dark at about 25° C., floral buds of the plant host to be transformed, which have been grown until the development of immature floral buds, are immersed in the bacterial suspension for 10 seconds, and then left to stand overnight with a cover to keep humidity; the cover is removed on the next day, the plants are allowed to grow and then seeds are harvested; transformed individuals can be selected by seeding harvested seeds on a solid medium supplemented with an appropriate selection marker such as an antibiotic; the thus selected individuals are transplanted into soil and allowed to grow, so that next-generation seeds of the transgenic plants can be obtained.

Progeny plants having a novel phenotype similar to that of transgenic plants can be produced by crossing the transgenic plants with wild-type plants.

The transgenic plants or progeny plants thereof produced by the above method are characterized in that they contain, in an expressible manner, DNA encoding a protein selected from the group consisting of a combination of TED6 and TED7, a C-terminal fragment of TED6, a C-terminal fragment of TED7, and a combination of a C-terminal fragment of TED6 and a C-terminal fragment of TED7, and that the thickness of the secondary cell walls is increased as compared with wild-type plants.

Accordingly, the present invention further provides not only such a transgenic plant or a progeny plant thereof, but also a cell or tissues or a seed therefrom.

Examples of subject plants of the present invention include, but are not limited to, plants, such as dicotyledons, monocotyledons, gymnosperms, and trees. Examples of particularly useful plants include arboreous plants and herbaceous plants that are important as biomass resources such as Eucalyptus, poplar, sugarcane, rice, and the Pooideae family.

(Secondary Cell Wall Formation—Promoting Functions of TED6 and TED7)

The present inventors have assumed in the course of the study using *Arabidopsis thaliana* that both TED6 and TED7 might be involved in the secondary cell wall synthesis of vessels (T. Demura, "Regulatory Mechanisms Underlying Xylogenesis in *Arabidopsis*, as a Model for Wood Formation," Abstracts in FUNCFIBER 2008 International Symposium on the Biology and Biotechnology of Wood, page 12 (2008)). However, it has been revealed that TED6 or TED7 alone actually does not have a function of promoting the secondary cell wall formation.

The present inventors have found for the first time, using an RNA interference (RNAi) method, that a protein selected from the group consisting of a combination of TED6 and TED7, a C-terminal fragment of TED6, a C-terminal fragment of TED7, and a combination of a C-terminal fragment of TED6 and a C-terminal fragment of TED7 has a function of promoting the formation of secondary cell walls of vessel cells and wood fiber cells as described herein. These proteins, C-terminal fragments thereof, and examples thereof according to the present invention are as described above.

As revealed by the results of the analysis of intracellular localization, TED6 and TED7 proteins are mainly present in the plasma membranes of plant cells and are also present to some degree in cell walls. Among them, TED7 tends to be retained in cell walls at higher levels than TED6. This may be due to an interaction of the proline-rich N-terminal domain of TED7. Structurally, TED6 has a proline-rich N-terminal domain that is very shorter than that of TED7. Therefore, it is assumed that TED6 is unlikely to be retained in cell walls. Regarding TED6, the results of an experiment using *Arabidopsis thaliana* revealed that TED6 binds to an IRX3 subunit of cellulose synthase CesA. This is evidence demonstrating that TED6 interacts with a secondary cell wall-CesA complex.

EXAMPLES

The present invention will be described in more detail by way of Examples below, which should not be construed as limiting the scope of the present invention.

Example 1

Functional Analysis of Ze TED6 and Ze TED7 Genes in Tracheary Elements of Plants of the Genus *Zinnia elegans* (*Zinnia*)

Based on bioinformatics analysis (including SOSUI, TMHMM, and SignalP) of Ze TED6 and Ze TED7 proteins, both of these proteins were predicted to be "type I membrane proteins" (single transmembrane protein having an extracellular or lumenal N-terminus and a cytoplasmic C-terminus). The above proteins contain general single transmembrane domain-like hydrophobic regions (representing 23 out of 95 amino acids and 23 amino acids out of 300 amino acids of the Ze TED6 protein and the Ze TED7 protein, respectively). It was predicted that the C-termini thereof would be located on the cytoplasmic side. However, regarding the potential activity of these proteins, no functional domain has been predicted by ProDom, PROSITE, or Pfam. Only a Pro-rich region has been identified in the N-terminal region of the Ze TED7 protein. It is well known that, among extracellular plant proteins, Pro-rich sequences are hydroxyproline-rich glycoproteins (HRGPs). Ze TED7 might be an HRGP, although it does not have any repeated motif which is generally observed in the HRGP family.

The intracellular localization of Ze TED6 or Ze TED7 was experimentally examined by introducing into *Zinnia elegans* mesophylls by electroporation a plasmid encoding the protein with YFP (yellow fluorescent protein) fused to its C-terminus, which was driven by CaMV 35S promoter (Endo et al., (2008) Plant J. 53: 864-875). The fluorescence signal from each fusion protein was detected only in peripheral regions of the cells, indicating the localization of the protein in plasma membranes and/or cell walls. With plasmolyzing cells, it was clearly indicated that the proteins were localized mainly in plasma membranes and to some extent in cell walls. The Ze TED7-YFP fusion protein was retained in cell walls at higher levels than the Ze TED6-YFP fusion protein. This can be explained by the possible interaction between the Pro-rich N-terminal domain of the Ze TED7 protein and cell walls.

The effects of the overexpression of the full-length Ze TED6 or Ze TED7 protein on TE SCW (secondary cell wall) formation were examined using a dsRNA-mediated RNAi method based on the number of cells representing visible TE SCW. Moreover, a similar examination was performed for the C-terminal domains of these proteins, so that the functions of the above cytoplasmic domains in SCW formation were evaluated. As a result, when the C-terminal domain (not the full-length protein) was used alone, a slight, but a significant increase (increase by several percent as compared with the overexpressed GUS as a control) was found. Accordingly, low-density cell culture ($0.5 \times 10^5$ cells/mL$^{-1}$) was used in order to observe the positive effects on SCW formation. Such culture usually results in low-percentage SCW formation (less than 30%) in a control. It was thus confirmed that the percentage of SCW formation was increased with statistical significance with the use of the C-terminal domain (FIG. 1A and FIG. 1B). Similarly, the simultaneous overexpression of both the full-length Ze TED6 protein and the full-length Ze TED7 protein resulted in an increased percentage of SCW formation (FIG. 1C), indicating the functional interaction between the Ze TED6 protein and the Ze TED7 protein in SCW formation of TE.

Example 2

Functional Analysis of at TED6 and at TED7 in Plants Belonging to the Family Brassicaceae (*Arabidopsis*)

The homologs of Ze TED6 and Ze TED7 genes in *Arabidopsis* were found to be At1g43790 (At TED6) and At5g48920 (At TED7), respectively. The promoter activity of At TED6 and At TED7 were examined using 1 kb- and 0.5 kb-upstream sequences of At TED6 and At TED7. GUS reporter genes were ligated to these upstream sequences. Expression of the reporter transgene in adventitious shoots was limited to vessel elements undergoing differentiation for both genes, confirming the functional homology with Ze TED6 and Ze TED7. YFP reporter genes were ligated to the N-termini of coding sequences for At TED6 and At TED7, and then the genes were expressed under the control of their own promoters. At TED6 signals and TED7-YFP signals were specifically observed only beneath SCW generated in protoxylem and metaxylem vessel elements undergoing differentiation. Inconsistent localization of these signals was observed in some cases in metaxylem vessel elements, although the biological significance thereof remained unknown.

To examine the functions of At TED6 and At TED7, transgenic *Arabidopsis* having full length, C-terminus, or inverted repeat (RNAi) of At TED6 or At TED7 to which CaMV 35S promoter had been ligated was produced. However, no drastic morphological changes were observed expect for *Arabidopsis* having inverted repeat of At TED7.

The transgenic plants could not grow on germination medium, but they survived on callus induction medium. This indicated that the constitutive loss of the function of the At TED7 gene resulted in the death of adventitious shoots upon RNAi analysis.

To further examine the loss of the functions of At TED6 and At TED7. the SALK T-DNA database for insertion mutants was searched. No line could be obtained for At TED6, although T-DNA/transposon insertion lines (SALK_084115, SALK_089549 and SM_2_30444) could be obtained for At TED7. No insertion was observed in the coding region of At TED7, but an insertion was observed in the 5' or 3' flanking region of At TED7. These results demonstrated that the insertion did not result in a knockout mutant of At TED7.

Figure 3:
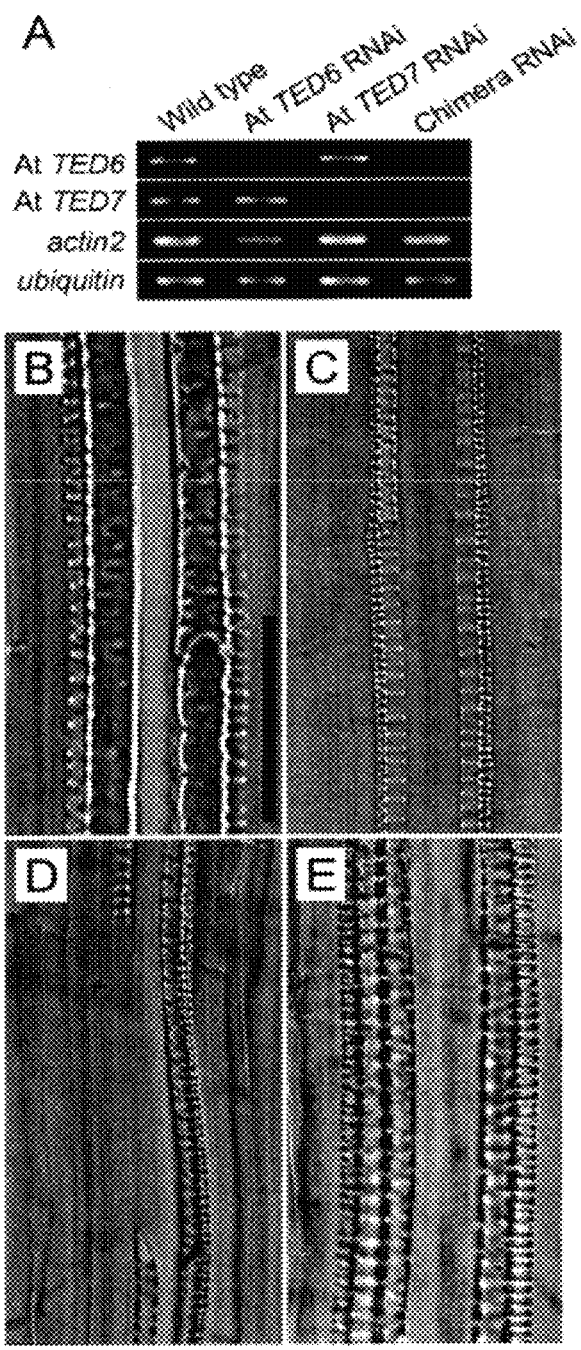
FIG. 3 shows the results of transient RNAi analysis of At TED6 and At TED7 genes in roots of *Arabidopsis thaliana*.

A dexamethasone (DEX)-inducible promoter (Aoyama and Chua (1997) Plant J. 11: 605-612) was used instead of constitutive RNAi of At TED7. An inverted repeat sequence of each of At TED6, At TED7, a chimera of At TED6 and At TED7, and YFP (control), to which the inducible promoter had been ligated, was introduced into an *Arabidopsis* plant. Transformants were selected by selecting plants that contains inducible RNAi constructs and that had sufficiently grown under non-induction conditions. Few transformants of At TED7 RNAi and At TED6-TED7 chimera RNAi could be obtained. This is considered to be due to the remaining "leakage" expression of the At TED7 inverted repeat that causes death in adventitious shoots. The efficiency of inducible RNAi was examined via RT-PCR for each target transcript in a juvenile plant line selected after 5 hours of exposure of plants to 10 μM dexamethasone (FIG. 3A). Inducible RNAi was performed for 3-week-old *Arabidopsis* plants by incubating the plants on growth medium supplemented with 10 μM dexamethasone for 5 days (FIG. 3B to FIG. 3E). It was unexpectedly revealed that DEX-inducible RNAi itself has unique effects including the formation of metaxylem vessels of roots having abnormally large pits on SCW and in some cases inhibition of the formation of protoxylem vessels of roots (FIG. 3E). In addition to the aforementioned unique effects, clear defects in SCW formation of the vessel elements of roots were caused in the inducible RNAi lines of At TED7 and At TED6-TED7 chimera (FIG. 3B and FIG. 3C). In both of these lines, abnormal vessel elements having unusual scalariform SCW (FIG. 3C) were formed instead of metaxylem vessels that usually form plexiform or pitted SCW (FIG. 3B). Furthermore, the At TED6-TED7 chimera RNAi line exhibited discontinuous or deficient vessels in metaxylem (FIG. 3D). Transmission electron microscopy of the roots of the At TED6-TED7 chimera RNAi line revealed that vessels having incomplete thin SCW (which is assumed to represent scalariform SCW) were located in the metaxylem, unlike the YFP RNAi control. These results strongly indicate the involvement of At TED6 and At TED7 in SCW formation of vessel elements.

Example 3 dsRNA and Plasmid DNA

*Zinnia* EST clones (Demura et al., 2002, Proc. Natl. Acad. Sci. U.S.A. 99: 15794-15799) was subjected to PCR to prepare a fragment containing T7 and SP6 promoters on both ends. The PCR product was purified and then directly used as a template for in vitro synthesis of dsRNA as described by Endo et al, (Plant J. 53: 864-875, 2008). The full-length cDNAs for Ze TED6 and Ze TED7 genes (clones Z1943 and Z16653, respectively) were obtained using a SMART RACE cDNA amplification kit (Clontech). The coding sequences were inserted into pH35GY (Kubo et al., 2005, Genes Dev. 19: 1855-1860) and pY35GS (Endo et al., 2008, Plant J. 53: 864-875) and the resultant constructs were used to examine protein localization and overexpression within *Zinnia* cells. pY35GUS which was constructed by insertion of GUS into pY35GS was used as a control. The sequence encoding $^{27}$Leu to $^{95}$Ala of Ze TED6 (SEQ ID NO: 1) and the sequence encoding $^{209}$Trp to $^{300}$Gly of Ze TED7 (SEQ ID NO: 2) were inserted into pY35GS. The sequences (1 kb and 0.5 kb, respectively) 5'-upstream of initiation codons of At TED6 and At TED7 genes were used as promoter regions. Fragments were inserted into pBGGUS (Kubo et al., 2005 (supra)) and then their promoter activities in *Arabidopsis* plants were examined. A genomic fragment containing a promoter region and ORF was inserted into pHGY (which was derived from pH35GY through deletion of the CaMV 35S promoter sequence). The first intron of a FAD2 (At3g12120) gene was used as a linker for inverted repeat sequences of full-length At TED6 ORF, At TED7 ORF, and At TED6-TED7 chimera sequence. At TED7 ORF was inserted to the PshA I site of At TED6 ORF, so as to construct a chimera. The inverted repeat was inserted into pH35GS (Kubo et al., 2005 (supra)) and/or pTA7002 (Aoyama and Chua, 1997, Plant J. 11: 605-612) to construct a vector for preparing a constitutive transient RNAi line. VND7 cDNA (Yamaguchi et al., 2008, Plant J. 55: 652-664) was inserted into pER8 (Zuo et al., 2000, Plant J. 24: 265273) to construct a vector for preparing an ectopic TE-inducible line.

(RT-PCR)

RNA was prepared from the two independent lines as described by Endo et al. (2008 (supra)) and then used for cDNA synthesis. PCR was performed using primers located in 5'- and 3'-UTRs of At TED6 and At TED7. Primers used for At TED6 were 5'-AGA GCC TCA CAC ATC AAA CAC AAG-3' (SEQ ID NO: 12) and 5'-GGT AAC ATT ATG AAT GAA GAA AGC TC-3' (SEQ ID NO: 13); primers used for At TED7 were 5'-AAC CAT TTA AGT ACA TAC ATA CTC CC-3' (SEQ ID NO: 14) and 5'-ATG ATT GTT TAC ATT TTG AGC CTT TTG-3' (SEQ ID NO: 15); primers used for actin 2 (At3g18780) were 5'-CCG TTT TGA ATC TTC CTC AAT C-3' (SEQ ID NO: 16) and 5'-ATA CCG GTA CCA TTG TCA CAC A-3' (SEQ ID NO: 17); and primers used for ubiquitin (At5g57860) were 5'-TCC AAT GTG ATC CAA CAG AGA C-3' (SEQ ID NO: 18) and 5'-TTC AAA GTC AAA GCC ACA ACT G-3' (SEQ ID NO: 19).

Furthermore, the following sequences were used for primers for PCR amplification of Ze TED7-1 and Ze TED7-2.

```
                                              (SEQ ID NO: 20)
    5'-TTC CCT CAT TTT CCA CCG CCA TC-3'
    and
                                              (SEQ ID NO: 21)
    5'-TGT TGT GGA ATG GTT GCT TGG AGA-3'
```

INDUSTRIAL APPLICABILITY

The present invention promotes the formation of secondary cell walls of vessel cells and wood fiber cells in plants and thus increases the thickness of secondary cell walls. The present invention enables increased cellulose content in arboreous plants and herbaceous plants which are biomass resources and therefore has a high degree of industrial usefulness.

All publications, patents, and patent applications cited herein are incorporated herein by reference in their entirety.
Sequence Listing Free Text
SEQ ID NOS: 12-21: primers
Sequencing Listing

The invention claimed is:

1. A method for increasing the thickness of a secondary cell wall of a plant, said method comprising producing a transgenic plant that contains expressible DNA encoding a protein consisting of a C-terminal domain of a tracheary element differentiation (TED) protein, wherein the C-terminal domain is selected from the group consisting of: amino acids 29-95 of SEQ ID NO: 1, amino acids 44-116 of SEQ ID NO: 4, amino acids 79-173 of SEQ ID NO: 6, amino acids 211-300 of SEQ ID NO: 2, amino acids 194-283 of SEQ ID NO: 3, amino acids 120-205 of SEQ ID NO: 5, amino acids 127-210 of SEQ ID NO: 7, amino acids 174-273 of SEQ ID NO: 8, amino acids 205-342 of SEQ ID NO: 9, and an amino acid sequence having at least 95% identity thereto; wherein the expressible DNA is expressed.

2. The method according to claim 1, wherein the expressible DNA encodes a protein consisting of a C-terminal domain of a TED protein, wherein the C-terminal domain is selected from the group consisting of: amino acids 29-95 of SEQ ID NO:1, amino acids 44-116 of SEQ ID NO: 4, amino acids 79-173 of SEQ ID NO: 6, and an amino acid sequence having at least 95% identity thereto; and
  also encodes a protein consisting of a C-terminal domain of a TED protein, wherein the C-terminal domain is selected from the group consisting of: amino acids 211-300 of SEQ ID NO: 2, amino acids 194-283 of SEQ ID NO: 3, amino acids 120-205 of SEQ ID NO: 5, amino acids 127-210 of SEQ ID NO: 7, amino acids 174-271 of SEQ ID NO: 8, amino acids 205-342 of SEQ ID NO: 9, and an amino acid sequence having at least 95% identity thereto.

3. A method for increasing the thickness of a secondary cell wall of a plant, said method comprising producing a transgenic plant that contains expressible DNA encoding a protein consisting of a C-terminal domain of a tracheary element differentiation (TED) protein, wherein the C-terminal domain is selected from the group consisting of: amino acids 29-95 of SEQ ID NO: 1, amino acids 44-116 of SEQ ID NO: 4, amino acids 79-173 of SEQ ID NO: 6, amino acids 211-300 of SEQ ID NO: 2, amino acids 194-283 of SEQ ID NO: 3, amino acids 120-205 of SEQ ID NO: 5, amino acids 127-210 of SEQ ID NO: 7, amino acids 174-273 of SEQ ID NO: 8, amino acids 205-342 of SEQ ID NO: 9, and an amino acid sequence having at least 95% identity thereto; wherein the expressible DNA encodes a protein that further comprises an additional 1 to 3 amino acids on the N-terminal side of the C-terminal domain of the TED protein.

4. A transgenic plant or a progeny plant thereof produced by the method of claim 1, wherein the thickness of the secondary cell wall is increased as compared to that of a wild-type plant; and wherein the progeny plant contains the expressible DNA.

5. The transgenic plant or progeny plant thereof according to claim 4, wherein the expressible DNA encodes a protein consisting of a C-terminal domain of a TED protein, wherein the C-terminal domain is selected from the group consisting of: amino acids 29-95 of SEQ ID NO: 1, amino acids 44-116 of SEQ ID NO: 4, amino acids 79-173 of SEQ ID NO: 6, and an amino acid sequence having at least 95% identity thereto;

and also encodes a protein consisting of a C-terminal domain of a TED protein, wherein the C-terminal domain is selected from the group consisting of: amino acids 211-300 of SEQ ID NO: 2, amino acids 194-283 of SEQ ID NO: 3, amino acids 120-205 of SEQ ID NO: 5, amino acids 127-210 of SEQ ID NO: 7, amino acids 174-271 of SEQ ID NO: 8, amino acids 205-342 of SEQ ID NO: 9, and an amino acid sequence having at least 95% identity thereto.

6. A cell or tissue of the transgenic plant or the progeny plant thereof according to claim 4, wherein the cell or tissue contains the expressible DNA.

7. A cell or tissue of the transgenic plant or the progeny plant thereof according to claim 5, wherein the cell or tissue contains the expressible DNA.

8. A seed of the transgenic plant or the progeny plant thereof according to claim 4, wherein the seed contains the expressible DNA.

9. A seed of the transgenic plant or the progeny plant thereof according to claim 5, wherein the seed contains the expressible DNA.

10. The method of claim 1, in which the expressible DNA encodes a protein consisting of a C-terminal domain of a TED protein, wherein the C-terminal domain is selected from the group consisting of: amino acids 29-95 of SEQ ID NO: 1, amino acids 44-116 of SEQ ID NO: 4, amino acids 79-173 of SEQ ID NO: 6, amino acids 211-300 of SEQ ID NO: 2, amino acids 194-283 of SEQ ID NO: 3, amino acids 120-205 of SEQ ID NO: 5, amino acids 127-210 of SEQ ID NO: 7, amino acids 174-273 of SEQ ID NO: 8, and amino acids 205-342 of SEQ ID NO: 9.

11. The method according to claim 1, wherein the expressible DNA encodes a protein consisting of a C-terminal domain of a TED protein, wherein the C-terminal domain is selected from the group consisting of: amino acids 29-95 of SEQ ID NO: 1, amino acids 44-116 of SEQ ID NO: 4, and amino acids 79-173 of SEQ ID NO: 6;

and also encodes a protein consisting of a C-terminal domain of a TED protein, wherein the C-terminal domain is selected from the group consisting of: amino acids 211-300 of SEQ ID NO: 2, amino acids 194-283 of SEQ ID NO: 3, amino acids 120-205 of SEQ ID NO: 5, amino acids 127-210 of SEQ ID NO: 7, amino acids 174-273 of SEQ ID NO: 8, and amino acids 205-342 of SEQ ID NO: 9.

12. The transgenic plant or a progeny plant thereof according to claim 4, that comprises an expressible DNA encoding a protein consisting of a C-terminal domain of a TED protein, wherein the C-terminal domain is selected from the group consisting of: amino acids 29-95 of SEQ ID NO: 1, amino acids 44-116 of SEQ ID NO: 4, amino acids 79-173 of SEQ ID NO: 6, amino acids 211-300 of SEQ ID NO: 2, amino acids 194-283 of SEQ ID NO: 3, amino acids 120-205 of SEQ ID NO: 5, amino acids 127-210 of SEQ ID NO: 7, amino acids 174-273 of SEQ ID NO: 8, and amino acids 205-342 of SEQ ID NO: 9.

* * * * *

SEQUENCE LISTING

```
<160> NUMBER OF SEQ ID NOS: 31

<210> SEQ ID NO 1
<211> LENGTH: 95
<212> TYPE: PRT
<213> ORGANISM: Zinnia elegans

<400> SEQUENCE: 1

Met Ala Thr Ile Phe Ile Val Phe Val Ser Phe Gly Cys Val Phe Val
1               5                   10                  15

Leu Gly Ile Ala Ala Phe Val Leu Cys Cys Leu Ile Lys Lys Trp Lys
            20                  25                  30

Cys Ser Lys Ala Ile Glu Lys Asn Glu Met Val His Val Asp Gln His
        35                  40                  45

Leu Gln Val His Glu Asn Ile Leu Gln Gly Pro Asn Gly Met Lys Thr
    50                  55                  60

Val Ala Ile Thr Val Asp Asp Leu His Val His Asp Glu Glu
65                  70                  75                  80

Cys Val Lys Asn Glu Lys Leu Gly Thr Ala Ser Thr Ser Lys Ala
                85                  90                  95

<210> SEQ ID NO 2
<211> LENGTH: 300
<212> TYPE: PRT
<213> ORGANISM: Zinnia elegans
```

<400> SEQUENCE: 2

Met Ala Ser Pro Leu Ser Gln Ser Val Phe Pro His Phe Pro Pro
1               5                   10                  15

Ser Pro Ala Ala Thr Pro Pro Ala Pro Thr Thr Pro Ser Thr Pro
            20                  25                  30

Pro Pro His Phe Ile Ser Pro Pro His Ser Val Pro Pro Pro Ser
            35                  40                  45

Pro Pro His Ser Val Pro Pro Leu His Pro Val Pro Pro Pro Ser
        50                  55                  60

Pro Pro His Pro Val Ser Pro Pro His Thr Val Pro Pro Pro Ser
65                  70                  75                  80

Pro Pro His Pro Val Ser Pro Pro His Thr Val Pro Pro Pro Ser
                85                  90                  95

Pro Pro His Pro Val Phe Pro Pro His Thr Val Pro Pro Pro Ser
            100                 105                 110

Pro His Phe Val Pro Pro Pro Asn Met Val Pro Pro Pro Ser Pro
            115                 120                 125

Pro His Ala Asn Pro Pro Pro Pro Pro His Ser Val Pro Pro
        130                 135                 140

Pro Pro His Thr Val Pro Pro Pro Pro Pro His Ile Ile Pro
145                 150                 155                 160

Pro Pro Ala His Ala Leu Ser Pro Pro Pro His Ile Ile Pro Pro
                165                 170                 175

Pro Pro Pro Ser Pro Ser Asn His Ser Thr Thr Ile Val Val Ile Phe
            180                 185                 190

Val Ser Cys Gly Gly Val Phe Phe Leu Ala Phe Ala Met Ala Ala Leu
                195                 200                 205

Trp Cys Phe Leu Lys Lys Lys Lys Lys Met Val Gln Lys Ala Glu
        210                 215                 220

Asn Ile His Phe Asp Glu His Arg Lys Val Thr Glu Arg Ile Glu Gln
225                 230                 235                 240

Gly Pro His Gly Thr Glu Thr Ala Ile Leu Ser Val Glu Asp Asp Ile
                245                 250                 255

His Ile Glu Glu Asp Ile Lys Lys Ser Glu Leu Glu Asn Phe Arg Lys
            260                 265                 270

Gly Leu His Leu Asn Tyr Gly Asn Thr Tyr Asn Ile Asp Thr Gly Lys
                275                 280                 285

Pro Ser Ser Ser Phe Gly His His Tyr Leu His Gly
        290                 295                 300

<210> SEQ ID NO 3
<211> LENGTH: 283
<212> TYPE: PRT
<213> ORGANISM: Zinnia elegans

<400> SEQUENCE: 3

Met Ala Ser His Leu Ser Gln Ser Leu Phe Pro His Phe Pro Pro
1               5                   10                  15

Ser Pro Ala Ala Thr Pro Pro Ala Pro Thr Thr Pro Ser Thr Pro
            20                  25                  30

Pro Pro His Phe Ile Ser Pro Pro His Ser Val Pro Pro Pro Ser
            35                  40                  45

Pro Pro His Ser Val Pro Pro Pro Leu His Pro Val Pro Pro Pro Leu
        50                  55                  60

```
Pro Pro His Ser Val Pro Pro Ser His Thr Val Pro Pro Ser
 65                  70                  75                  80

Pro Pro His Pro Val Ser Pro Pro His Thr Val Pro Pro Ser
                 85                  90                  95

Pro Pro His Pro Val Ser Pro Pro His Thr Val Pro Pro Ser
            100                 105                 110

Pro Pro His His Val Ser Pro Pro His Thr Val Pro Pro Ser
            115                 120                 125

Pro His Phe Val Pro Pro Pro Asn Thr Val Pro Pro Pro Ala
            130                 135                 140

Pro His Phe Val Pro Pro Pro Pro Tyr Ile Ile Pro Pro Pro
145                 150                 155                 160

Pro Pro Ser Pro Ser Asn His Ser Thr Thr Ile Val Ile Phe Val
                165                 170                 175

Ser Cys Gly Gly Val Phe Phe Leu Ala Phe Ala Met Ala Ala Leu Trp
                180                 185                 190

Cys Phe Leu Lys Lys Lys Lys Lys Met Val Arg Lys Ala Glu Asn
            195                 200                 205

Ile His Phe Asp Glu His Arg Lys Val Thr Glu Arg Ile Glu Gln Gly
        210                 215                 220

Pro His Gly Thr Glu Thr Ala Ile Leu Ser Val Glu Asp Ile His
225                 230                 235                 240

Ile Glu Glu Asp Ile Lys Lys Ser Glu Ile Glu Asp Phe Arg Lys Gly
                245                 250                 255

Leu His Leu Asn Tyr Gly Asn Thr Tyr Asn Ile Asp Thr Gly Lys Pro
            260                 265                 270

Ser Ser Ser Phe Gly His His Tyr Leu His Gly
            275                 280

<210> SEQ ID NO 4
<211> LENGTH: 116
<212> TYPE: PRT
<213> ORGANISM: Arabidopsis thaliana

<400> SEQUENCE: 4

Met Ala Ser Thr Asp Ser Val Tyr Arg Pro Thr Pro Thr Pro Asp His
  1               5                  10                  15

Asp Thr Thr Val Val Val Val Phe Val Ser Leu Gly Cys Val Met
                 20                  25                  30

Phe Leu Ala Phe Leu Ala Phe Val Ile Trp Phe Leu Ile Lys Lys Arg
             35                  40                  45

Ser Arg Lys His Arg Glu Arg Ser Glu Ala Val Arg Val Asp Glu His
 50                  55                  60

Phe Lys Met Lys Glu Ala Ile Val Glu Gly Pro Asn Gly Gln Lys Ser
 65                  70                  75                  80

Val Val Leu Ser Val Glu Asp Asp Val Lys Ile Glu Asp Ala Ile Lys
                 85                  90                  95

Arg Glu Glu Lys Asp Leu Lys Lys Asp Gly Gly Val Gly Ser Ser Val
            100                 105                 110

Val Ser Arg Ser
            115

<210> SEQ ID NO 5
<211> LENGTH: 205
<212> TYPE: PRT
<213> ORGANISM: Arabidopsis thaliana
```

<400> SEQUENCE: 5

```
Met Ala Ala Ser Val Glu Tyr Phe Pro Tyr Ser Pro Pro Ser His
1               5                   10                  15

Gln His Pro Leu Pro Ser Pro Val Pro Pro Pro Ser His Ile Ser
            20                  25                  30

Pro Pro Pro Pro Pro Phe Ser Pro Pro His His Pro Pro Pro His
        35                  40                  45

Phe Ser Pro Pro His Gln Pro Pro Ser Pro Tyr Pro His Pro His
    50                  55                  60

Pro Pro Pro Pro Ser Pro Tyr Pro His Pro His Gln Pro Pro Pro
65                  70                  75                  80

Pro His Val Leu Pro Pro Pro Pro Thr Pro Ala Pro Gly His His
                85                  90                  95

Val Ile Ile Val Val Val Ile Ser Leu Gly Ser Leu Phe Phe Leu Ala
            100                 105                 110

Phe Leu Ala Ala Ala Leu Phe Cys Tyr Leu Lys Lys Arg Arg Lys Ser
        115                 120                 125

Ser Thr Lys Ala Glu Ile Ile Glu Phe Asp Glu His Leu Lys Val Gln
    130                 135                 140

Glu Thr Ile Val Gln Gly Pro His Gly Glu Gln Thr Arg Val Val Met
145                 150                 155                 160

Leu Glu Glu Asp Ile His Leu Val Glu Asp Ile His Lys Thr Glu Lys
                165                 170                 175

Leu Ser Arg Pro Ser His Leu Ser Thr Gly Arg His Ala Ile Asp
            180                 185                 190

Ile Ser Asp Pro Asn His His Phe Thr Glu Gln Lys Ser
        195                 200                 205
```

<210> SEQ ID NO 6
<211> LENGTH: 173
<212> TYPE: PRT
<213> ORGANISM: Populus trichocarpa

<400> SEQUENCE: 6

```
Met Ala Ala Ser Asn Asn Leu Asp Phe Pro Tyr Ser Pro Pro Pro Pro
1               5                   10                  15

Ser His Ser Phe Gln Pro Pro Ser Pro Pro His Val Arg Pro Pro
            20                  25                  30

Pro Pro His Ile Arg Pro Pro Pro Pro Leu Pro Pro Ala Pro Ser
        35                  40                  45

Pro Ser Asn Asn Thr Thr Val Ile Val Ile Val Phe Val Ser Phe Gly
    50                  55                  60

Gly Leu Ile Phe Leu Ala Phe Leu Ala Ala Leu Cys Phe Phe Ile
65                  70                  75                  80

Lys Lys Lys Lys Lys Lys Thr Val Glu Glu Thr Asp Ile Val His Val
                85                  90                  95

His Glu His Leu Lys Val Lys Glu Ala Ile Val Glu Gly Pro His Gly
            100                 105                 110

Pro Lys Ala Val Val Leu Glu Ile Val Asp Asp Val His Ile Gly Glu
        115                 120                 125

Glu Ile Lys Glu Glu Glu Lys Val Gly Glu Gly Leu His Ala Lys Ala
    130                 135                 140
```

```
Ile Glu Gly Asn Ala Gly Thr Val Asp Gln Leu Ala Ala Pro Ser Ser
145                 150                 155                 160

Ser Gly Ser Asn Asn His Ser Arg Leu Glu His Lys Ala
                165                 170
```

<210> SEQ ID NO 7
<211> LENGTH: 210
<212> TYPE: PRT
<213> ORGANISM: Populus trichocarpa

<400> SEQUENCE: 7

```
Met Ala Pro Thr Asn Asn Tyr Asp Tyr Asn Phe Pro Tyr Phe Pro Leu
1               5                   10                  15

Pro Pro Pro His Asn Asn Pro Pro Ser Pro Pro Lys Val Ala Pro Pro
                20                  25                  30

His Ser Ser Pro Ser Pro Pro Asn Val Ser Pro His Asn Phe Pro
                35                  40                  45

Pro Pro His Ile Thr Pro Pro Ser Pro Lys Val Pro Pro Pro Pro His
            50                  55                  60

His Pro Ile Thr Pro Pro Thr His Pro Phe His Pro Pro Pro
65                  70                  75                  80

His His Ile Pro Pro Pro His Val Ile Pro Pro Pro Pro Thr
                    85                  90                  95

Pro Gly His His Ser Thr Val Ile Ile Val Val Phe Val Ser Leu Gly
                100                 105                 110

Gly Leu Phe Phe Leu Ala Phe Leu Ser Val Ala Leu Cys Cys Phe Ile
            115                 120                 125

Lys Lys Lys Lys Lys Lys Thr Val Gln Lys Thr Glu Ile Leu Glu Phe
130                 135                 140

Asp Glu His Thr Lys Val Gln Glu Ala Ile Val Pro Gly Pro His Gly
145                 150                 155                 160

Glu Lys Ile Thr Val Leu Asn Ile Glu Glu Asp Val His Leu Val Glu
                165                 170                 175

Glu Ile Lys Lys Asn Glu Lys Leu Thr Glu Gly Ser His Ile Lys Ser
            180                 185                 190

Ala His Asp Arg Pro Leu Tyr Ser Asp Ile Ala Thr Pro Ser Ser Gln
                195                 200                 205

Tyr Asn
    210
```

<210> SEQ ID NO 8
<211> LENGTH: 273
<212> TYPE: PRT
<213> ORGANISM: Populus trichocarpa

<400> SEQUENCE: 8

```
Met Ala Pro Leu Asp Asn Tyr Asp Tyr Asn Phe Pro Tyr Phe Pro Leu
1               5                   10                  15

Pro Pro Pro His Asn Pro Pro Ser Pro Pro Lys Val Val Pro Pro His
                20                  25                  30

Asn Tyr Pro Ser Pro Pro Lys Gly Ser Pro Pro His Asn Pro Pro Pro
                35                  40                  45

Pro His Ile Ile Pro Ser Pro Pro Lys Val Val Pro Pro His Asn Tyr
            50                  55                  60

Pro Ser Pro Pro Lys Gly Ser Pro Pro His Asn Pro Pro Pro His
65                  70                  75                  80
```

```
Ile Lys Pro Ser Pro Lys Val Pro Pro His His Pro Ile Thr
                85              90              95
Pro Pro Ser Pro Phe Pro Val Pro Ala Thr Pro Asn His Pro Phe
            100             105             110
His Pro Pro Pro His His Ile Pro Pro Ser Pro Pro His Ile
            115             120             125
Ile Pro Pro Ala Pro Ser His Val Ile Pro Pro Pro Thr Pro
    130             135             140
Gly His His Ser Thr Val Ile Ile Val Val Phe Val Ser Leu Gly Gly
145             150             155             160
Leu Phe Phe Leu Ala Phe Leu Ser Val Ala Leu Cys Cys Phe Ile Lys
                165             170             175
Lys Lys Lys Lys Lys Thr Val Gln Lys Thr Glu Ile Leu Glu Phe Asp
                180             185             190
Glu His Thr Lys Val Gln Glu Ala Ile Ile Pro Gly Pro His Gly Glu
            195             200             205
Lys Ile Thr Val Leu Asn Ile Glu Glu Asp Val His Leu Val Glu Glu
    210             215             220
Ile Lys Lys Asn Glu Lys Leu Ala Glu Gly Ser His Ile Lys Leu Ala
225             230             235             240
His Asp His Pro Leu Asp Ser Asp Ile Ala Thr Ser Ser Ser Arg Ser
                245             250             255
Asn Gln Gln His Leu Glu His Lys Val Gln His His Leu Glu His Lys
            260             265             270
Val

<210> SEQ ID NO 9
<211> LENGTH: 342
<212> TYPE: PRT
<213> ORGANISM: Oryza sativa

<400> SEQUENCE: 9

Met Thr Phe Asn Pro Gly Ser Pro Gly Phe Gly Phe Pro Phe Pro Phe
1               5               10              15
Tyr Pro Pro Asn Pro Asn Pro Tyr Ala Pro Leu Asn Pro Asn Ala Pro
                20              25              30
Lys Pro Pro Val Met Pro Pro Arg Pro Gln Ala Pro Pro Pro Pro Gln
            35              40              45
Arg Phe Pro Pro Pro Ala Pro Pro Ile Arg Pro Ser Pro Pro
    50              55              60
Gly Arg Ala Pro Pro Pro Gly Arg Ala Pro Pro Pro Pro Ser Gln
65              70              75              80
Ala Pro Pro Pro Arg Arg Ala Pro Pro Pro Ala Leu Pro Pro
                85              90              95
Pro Pro Pro Arg Arg Ala Pro Pro Pro Ser Met Pro Pro Pro
            100             105             110
Pro Pro Arg Arg Ala Pro Pro Pro Ala Thr Pro Pro Pro Pro
            115             120             125
Arg Arg Ala Pro Pro Pro Ser Pro Pro Ile Arg Pro Pro Pro Pro
130             135             140
Pro Thr Pro Arg Pro Tyr Ala Pro Pro Pro Ser His Pro Leu Ala
145             150             155             160
Pro Pro Pro Pro His Ile Ser Pro Pro Ala Pro Val Pro Pro Pro
                165             170             175
```

```
Ser Pro Pro Pro His Ile Val Ile Ile Val Phe Val Ser Phe Gly
            180                 185                 190
Gly Leu Leu Leu Leu Ala Cys Leu Ala Ala Leu Phe Cys Trp His Lys
        195                 200                 205
Lys Arg Arg Glu Thr Glu Arg Lys Ala Glu Val His Asn Leu Ser Gly
        210                 215                 220
His Val His Val His Lys Ala Thr Glu Ser Gly Pro Ser Gly Ala Lys
225                 230                 235                 240
Ala Thr Val Leu Ser Ile Asp Glu Asp Leu Lys Phe Gln Glu Val Ala
                245                 250                 255
Gly Glu Ser Ser Ser Ala Ala Gly Ala Gly Ser His His Thr Pro Trp
            260                 265                 270
Ser Trp His Arg Arg Gln Gln Glu Gly Lys Ala Glu Asn Lys Ala Glu
        275                 280                 285
Leu Ile Asn Val Thr Glu His Ile His Val Asp Glu Lys Ile Val Ser
        290                 295                 300
Gly Pro Gln Gly Gln Lys Ile Glu Ile Leu Ser Glu Asp Glu Asp Ile
305                 310                 315                 320
Arg Phe Glu Glu Glu Gly Arg Lys Glu Lys Gly Asp Gln Arg Ser Lys
                325                 330                 335
Thr Arg Ile Thr Lys Thr
            340
```

<210> SEQ ID NO 10
<211> LENGTH: 45
<212> TYPE: PRT
<213> ORGANISM: Oryza sativa

<400> SEQUENCE: 10

```
Thr Glu Arg Lys Ala Glu Val His Asn Leu Ser Gly His Val His Val
1               5                   10                  15
His Lys Ala Thr Glu Ser Gly Pro Ser Gly Ala Lys Ala Thr Val Leu
            20                  25                  30
Ser Ile Asp Glu Asp Leu Lys Phe Gln Glu Val Ala Gly
        35                  40                  45
```

<210> SEQ ID NO 11
<211> LENGTH: 45
<212> TYPE: PRT
<213> ORGANISM: Oryza sativa

<400> SEQUENCE: 11

```
Ala Glu Asn Lys Ala Glu Leu Ile Asn Val Thr Glu His Ile His Val
1               5                   10                  15
Asp Glu Lys Ile Val Ser Gly Pro Gln Gly Gln Lys Ile Glu Ile Leu
            20                  25                  30
Ser Glu Asp Glu Asp Ile Arg Phe Glu Glu Glu Gly Arg
        35                  40                  45
```

<210> SEQ ID NO 12
<211> LENGTH: 24
<212> TYPE: DNA
<213> ORGANISM: Artificial
<220> FEATURE:
<223> OTHER INFORMATION: primer

<400> SEQUENCE: 12
agagcctcac acatcaaaca caag                                        24

```
<210> SEQ ID NO 13
<211> LENGTH: 26
<212> TYPE: DNA
<213> ORGANISM: Artificial
<220> FEATURE:
<223> OTHER INFORMATION: primer

<400> SEQUENCE: 13
ggtaacatta tgaatgaaga aagctc                                          26

<210> SEQ ID NO 14
<211> LENGTH: 26
<212> TYPE: DNA
<213> ORGANISM: Artificial
<220> FEATURE:
<223> OTHER INFORMATION: primer

<400> SEQUENCE: 14
aaccatttaa gtacatacat actccc                                          26

<210> SEQ ID NO 15
<211> LENGTH: 27
<212> TYPE: DNA
<213> ORGANISM: Artificial
<220> FEATURE:
<223> OTHER INFORMATION: primer

<400> SEQUENCE: 15
atgattgttt acattttgag ccttttg                                         27

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
ccgttttgaa tcttcctcaa tc                                              22

<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
ataccggtac cattgtcaca ca                                              22

<210> SEQ ID NO 18
<211> LENGTH: 22
<212> TYPE: DNA
<213> ORGANISM: Artificial
<220> FEATURE:
<223> OTHER INFORMATION: primer

<400> SEQUENCE: 18
tccaatgtga tccaacagag ac                                              22

<210> SEQ ID NO 19
<211> LENGTH: 22
<212> TYPE: DNA
<213> ORGANISM: Artificial
<220> FEATURE:
<223> OTHER INFORMATION: primer
```

<400> SEQUENCE: 19
ttcaaagtca aagccacaac tg                                              22

<210> SEQ ID NO 20
<211> LENGTH: 23
<212> TYPE: DNA
<213> ORGANISM: Artificial
<220> FEATURE:
<223> OTHER INFORMATION: primer

<400> SEQUENCE: 20
ttccctcatt ttccaccgcc atc                                             23

<210> SEQ ID NO 21
<211> LENGTH: 24
<212> TYPE: DNA
<213> ORGANISM: Artificial
<220> FEATURE:
<223> OTHER INFORMATION: primer

<400> SEQUENCE: 21
tgttgtggaa tggttgcttg gaga                                            24

<210> SEQ ID NO 22
<211> LENGTH: 45
<212> TYPE: PRT
<213> ORGANISM: Arabidopsis thaliana

<400> SEQUENCE: 22

His Arg Glu Arg Ser Glu Ala Val Arg Val Asp Glu His Phe Lys Met
1               5                   10                  15

Lys Glu Ala Ile Val Glu Gly Pro Asn Gly Gln Lys Ser Val Val Leu
            20                  25                  30

Ser Val Glu Asp Asp Val Lys Ile Glu Asp Ala Ile Lys
        35                  40                  45

<210> SEQ ID NO 23
<211> LENGTH: 45
<212> TYPE: PRT
<213> ORGANISM: Populus trichocarpa

<400> SEQUENCE: 23

Thr Val Glu Glu Thr Asp Ile Val His Val His Glu His Leu Lys Val
1               5                   10                  15

Lys Glu Ala Ile Val Glu Gly Pro His Gly Pro Lys Ala Val Val Leu
            20                  25                  30

Glu Ile Val Asp Asp Val His Ile Gly Glu Glu Ile Lys
        35                  40                  45

<210> SEQ ID NO 24
<211> LENGTH: 45
<212> TYPE: PRT
<213> ORGANISM: Zinnia elegans

<400> SEQUENCE: 24

Ala Ile Glu Lys Asn Glu Met Val His Val Asp Gln His Leu Gln Val
1               5                   10                  15

His Glu Asn Ile Leu Gln Gly Pro Asn Gly Met Lys Thr Val Ala Ile
            20                  25                  30

Thr Val Asp Asp Asp Leu His Val His Asp Glu Glu Glu
        35                  40                  45

<210> SEQ ID NO 25
<211> LENGTH: 45
<212> TYPE: PRT
<213> ORGANISM: Zinnia elegans

<400> SEQUENCE: 25

Met Val Gln Lys Ala Glu Asn Ile His Phe Asp Glu His Arg Lys Val
1               5                   10                  15

Thr Glu Arg Ile Glu Gln Gly Pro His Gly Thr Glu Thr Ala Ile Leu
            20                  25                  30

Ser Val Glu Asp Asp Ile His Ile Glu Glu Asp Ile Lys
        35                  40                  45

<210> SEQ ID NO 26
<211> LENGTH: 45
<212> TYPE: PRT
<213> ORGANISM: Zinnia elegans

<400> SEQUENCE: 26

Met Val Arg Lys Ala Glu Asn Ile His Phe Asp Glu His Arg Lys Val
1               5                   10                  15

Thr Glu Arg Ile Glu Gln Gly Pro His Gly Thr Glu Thr Ala Ile Leu
            20                  25                  30

Ser Val Glu Asp Asp Ile His Ile Glu Glu Asp Ile Lys
        35                  40                  45

<210> SEQ ID NO 27
<211> LENGTH: 45
<212> TYPE: PRT
<213> ORGANISM: Populus trichocarpa

<400> SEQUENCE: 27

Thr Val Gln Lys Thr Glu Ile Leu Glu Phe Asp Glu His Thr Lys Val
1               5                   10                  15

Gln Glu Ala Ile Val Pro Gly Pro His Gly Glu Lys Ile Thr Val Leu
            20                  25                  30

Asn Ile Glu Glu Asp Val His Leu Val Glu Glu Ile Lys
        35                  40                  45

<210> SEQ ID NO 28
<211> LENGTH: 45
<212> TYPE: PRT
<213> ORGANISM: Populus trichocarpa

<400> SEQUENCE: 28

Thr Val Gln Lys Thr Glu Ile Leu Glu Phe Asp Glu His Thr Lys Val
1               5                   10                  15

Gln Glu Ala Ile Ile Pro Gly Pro His Gly Glu Lys Ile Thr Val Leu
            20                  25                  30

Asn Ile Glu Glu Asp Val His Leu Val Glu Glu Ile Lys
        35                  40                  45

<210> SEQ ID NO 29
<211> LENGTH: 45
<212> TYPE: PRT
<213> ORGANISM: Arabidopsis thaliana

```
<400> SEQUENCE: 29

Ser Ser Thr Lys Ala Glu Ile Ile Glu Phe Asp Glu His Leu Lys Val
1               5                   10                  15

Gln Glu Thr Ile Val Gln Gly Pro His Gly Glu Gln Thr Arg Val Val
                20                  25                  30

Met Leu Glu Glu Asp Ile His Leu Val Glu Asp Ile His
            35                  40                  45

<210> SEQ ID NO 30
<211> LENGTH: 45
<212> TYPE: PRT
<213> ORGANISM: Oryza sativa

<400> SEQUENCE: 30

Thr Glu Arg Lys Ala Glu Val His Asn Leu Ser Gly His Val His Val
1               5                   10                  15

His Lys Ala Thr Glu Ser Gly Pro Ser Gly Ala Lys Ala Thr Val Leu
                20                  25                  30

Ser Ile Asp Glu Asp Leu Lys Phe Gln Glu Val Ala Gly
            35                  40                  45

<210> SEQ ID NO 31
<211> LENGTH: 45
<212> TYPE: PRT
<213> ORGANISM: Oryza sativa

<400> SEQUENCE: 31

Ala Glu Asn Lys Ala Glu Leu Ile Asn Val Thr Glu His Ile His Val
1               5                   10                  15

Asp Glu Lys Ile Val Ser Gly Pro Gln Gly Gln Lys Ile Glu Ile Leu
                20                  25                  30

Ser Glu Asp Glu Asp Ile Arg Phe Glu Glu Glu Gly Arg
            35                  40                  45
```